United States Patent [19]

Thalhammer et al.

[11] Patent Number: 5,688,947
[45] Date of Patent: Nov. 18, 1997

[54] PRODUCTION OF PURINES VIA REDUCTIVE FORMYLATION

[75] Inventors: Franz Thalhammer; Jürgen Graefe, both of Trostberg, Germany

[73] Assignee: Skw Trostberg Aktiengesellschaft, Trostberg, Germany

[21] Appl. No.: 495,051

[22] Filed: Jun. 26, 1995

[30] Foreign Application Priority Data

Jun. 28, 1994 [DE] Germany .................... 44 22 587.3

[51] Int. Cl.$^6$ ............ C07D 473/18; C07D 473/16; C07D 473/04; C07D 473/20
[52] U.S. Cl. ............ 544/264; 544/265; 544/273; 544/276; 544/277
[58] Field of Search .................. 544/264, 265, 544/273, 276, 277

[56] References Cited

U.S. PATENT DOCUMENTS 4,286,093  8/1981  Temple, Jr. .................... 544/276

FOREIGN PATENT DOCUMENTS

| 0267594 | 5/1988 | European Pat. Off. . |
| 0541003 | 5/1988 | European Pat. Off. . |
| 0304004 | 2/1989 | European Pat. Off. . |
| 0415028 | 7/1990 | European Pat. Off. . |
| 3729471 | 3/1989 | Germany . |

OTHER PUBLICATIONS

Shin Ozuka, Inorganica Chimica Acta 100, 141 (1985).

Primary Examiner—Mark L. Berch
Attorney, Agent, or Firm—Felfe & Lynch

[57] ABSTRACT

In order to produce a purine of the general formula (I),

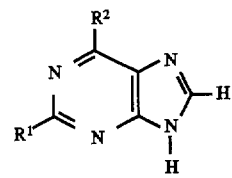

in which $R^1$ and $R^2$ can be the same or different and denote H, OH, SH, $NH_2$, N-(di)-alkyl, halogen, O-alkyl, S-alkyl, alkyl or aryl and alkyl represents an aliphatic residue with 1 to 4 carbon atoms and aryl represents a phenyl residue which is substituted if desired by $CH_3$, OH, $NH_2$ or halogen, from the corresponding 4-amino-5-nitrosopyrimidine of formula (II),

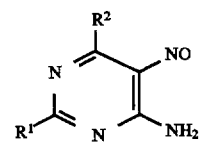

in which $R^1$ and $R^2$ have the above-mentioned meaning, the compound of formula (II) is reductively formylated in a solvent at a temperature of 80° to 220° C. in the presence of formic acid and a catalyst based on a noble metal and the 4-amino-5-formylaminopyrimidine formed as an intermediate is cyclized.

25 Claims, No Drawings

PRODUCTION OF PURINES VIA REDUCTIVE FORMYLATION

DESCRIPTION

The invention concerns a process for the production of purines from the corresponding 4-amino-5-nitrosopyrimidines by reductive formylation and subsequent cyclization of the 4-amino-5-formylaminopyrimidines which are formed as intermediates.

Purines have previously mainly been produced from salts of 4,5-diamino-pyrimidines or from 4-amino-5-(formylamino)pyrimidines. For example according to EP-A 415 028 guanine is obtained by heating 2,4,5-triamino-6-hydroxypyrimidine sulfate (TAHP sulfate) with sodium formate in formic acid.

According to DE-PS 37 29 471, guanine is obtained by heating TAHP sulfate in formamide during which ammonia, as the decomposition product of formamide, neutralizes the sulfate. These processes have the disadvantage that they require 4,5-diaminopyrimidines as starting materials which are produced from the corresponding 5-nitrosopyrimidines by catalytic hydrogenation with hydrogen for example by analogy to DE-PS 36 38 635 which requires expensive autoclaves or loop-type reactors. In addition the unstable 4,5-diaminopyrimidines must be converted into the sulfate form for stabilization. This leads to a high amount of salt formed which is disadvantageous with regard to cost-efficiency and ecological balance.

The production of 2,4-diamino-5-formylamino-6-hydroxypyrimidine (DAFHP) by catalytic hydrogenation of the corresponding nitroso compounds with hydrogen and subsequent formylation is described in DE-PS 36 38 635. According to DE-OS 41 36 114 DAFHP can be converted in formamide to guanine. In all of these processes it is necessary to isolate and possible purify the precursor which is why purines must be accordingly produced in two separate process steps from the corresponding 5-nitrosopyrimidines.

Finally a one-pot process for the production of the sodium salts of purines is known from EP-A 304 004. According to this process 4-amino-5-nitrosopyrimidines are produced from 4-aminopyrimidines by nitrosation in formamide, these are reduced with sodium dithionite, subsequently formylated with formic acid and finally cyclized at increased temperatures to form the corresponding purines. A disadvantage of this process is that salts containing sulphur are formed as a result of the use of sodium dithionite and in addition $SO_2$ is released in large amounts. Therefore this process is not acceptable on a large technical scale from an ecological point of view.

The object of the present invention is therefore to create a process for the production of purines of the general formula (I),

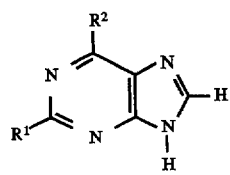

in which $R^1$ and $R^2$ can be the same or different and denote H, OH, SH, $NH_2$, N-(di)-alkyl, halogen, O-alkyl, S-alkyl, alkyl or aryl and alkyl represents an aliphatic residue with 1 to 4 carbon atoms and aryl represents a phenyl residue which is substituted if desired with $CH_3$, OH, $NH_2$ or halogen, from the corresponding 4-amino-5-nitrosopyrimidines which does not have the aforementioned disadvantages of the state of the art but which enables production of the desired purines without any difficulties, without being technically complex and in particular without requiring elemental hydrogen or the ecologically unacceptable sodium dithionite.

This object is achieved according to the invention by reductively formylating the 4-amino-5-nitrosopyrimidine of the general formula (II), in which $R^1$ and $R^2$ have the above-mentioned meaning, in the presence of formic acid and a catalyst based on a noble metal in a solvent at a temperature of 80° to 220° C. and cyclizing the 4-amino-5-formylaminopyrimidine that is formed as an intermediate.

It surprisingly turned out that, according to the invention, purines of the general formula (I) can be obtained in a one-pot process in high yields and good purities wherein formic acid functions simultaneously as a reducing and formylation reagent and moreover, if necessary also as a solvent. In addition the noble metal catalyst does not have to be separated before the ring closure reaction to form the purines which was also not foreseeable. In the process of the invention a 4-amino-5-nitrosopyrimidine of the general formula (II) is used

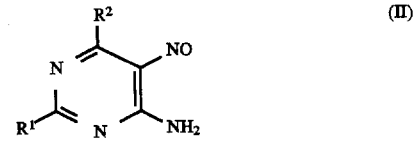

in which the residues $R^1$ and $R^2$ are the same or different and denote H, OH, SH, $NH_2$, N-(di)-alkyl, halogen, O-alkyl, S-alkyl, alkyl or aryl and alkyl represents an aliphatic residue with 1 to 4 carbon atoms. This starting compound is suspended in a solvent which is preferably composed of formic acid and/or formamide. According to a preferred embodiment the 4-amino-5-nitrosopyrimidine is used after it has been produced by nitrosation from 4-aminopyrimidines in a water-wet form or even in the reaction suspension which occurs.

The concentration of the nitroso compound of formula (II) in the solvent can be varied within wide limits and is 0.1 to 3.0, preferably 1.0 to 2.0 mol per liter solvent. If formamide is used as the solvent, formic acid must be added to the reaction mixture and namely in particular 2.0 to 10.0 mole, preferably 3.5 to 5.0 mole formic acid per mole nitroso compound of formula (II). Alternatively formic acid itself can be used as the solvent if desired in an aqueous dilution of up to 20% by weight. In order to accelerate the reaction and to improve the stirrability of highly concentrated mixtures, a salt of formic acid, in particular a formate of alkali and alkaline-earth metals, of ammonia or amines can be added to the reaction mixture. In this connection sodium, ammonium and triethylammonium formate are preferred in which a molar ratio of 0.1 to 5, particularly preferably of about 0.5 in relation to the amount of added nitroso compound of formula (II) is used. The formate can be added in a solid or dissolved form.

A noble metal catalyst is added to the reaction mixture produced in this manner. A catalyst based on palladium, platinum, ruthenium or rhodium, preferably on a carrier material and in particular on active carbon, is preferably added. Commercial products are suitable. The noble metal content of the catalyst is advantageously 0.1 to 10% by weight. A catalyst containing about 5% by weight palladium on active carbon has proven to be particularly suitable. The catalyst is preferably used in such an amount that the proportion of pure noble metal is 20 to 2000 mg, particularly preferably 100 to 500 mg per kilogram of nitroso compound of formula (II) used.

After addition of the catalyst $CO_2$ starts to be slowly released while stirring, even at room temperature. Subsequently the desired reaction temperature is set. Preferably the temperature is adjusted to 80° to 140° C., in particular 100° to 120° C. during a first period of 1 to 4 hours. During this period there is a decolorization of the suspension which at first is colored a deep red to violet. Subsequently when using formamide as the solvent, the temperature, is preferably increased to 150° to 190° C. during which reaction water which may be formed is removed by distillation if necessary. When formic acid is used as the solvent the temperature is preferably increased to 100° to 170° C. In this process temperatures above about 110° C. require the application of pressures of up to about 20 bar. It is also possible to reach higher temperatures by admixing high-boiling solvents such as e.g. glycol ethers, diphenyl ethers etc. However, this requires a complicated distillative recovery of the respective solvent at the end of the production of the respective purine.

The duration of heating depends on the level of the reaction temperature. In formamide about 10 hours at 160° C. or about 3 hours at 180° C. are necessary. If formic acid is used the reaction period is about 20 hours at 110° C. or ca. 2 hours at 160° C. under a pressure of 8 bar.

The suspension of the purine obtained in this manner contains no detectable amounts of the starting compound or of 4-amino-5-formylaminopyrimidine. However, the purine is partially present as the formate. In addition formic acid salts and the noble metal catalyst which may have been added as well as small amounts of colored decomposition products are still present.

In order to isolate the purine and to recover the noble metal catalyst, it is expedient to cool and filter the suspension. In order to improve the filterability of very viscous suspensions, water or an organic solvent can be added which can then again easily be removed from the mother liquor by distillation e.g. acetone, methanol or acetonitrile.

In this procedure the purine together with the noble metal catalyst are removed by filtration and washed with water. The filter cake can then be taken up in 5 to 10% by weight sodium hydroxide solution during which the catalyst remains undissolved and can be separated by filtration.

In this way the added noble metal catalyst is advantageously recovered almost quantitatively which is useful for an economic process due to the high price of the noble metal. Surprisingly the catalyst also substantially retains its activity despite the extreme temperature stress so that it can be used again in subsequent reactions.

In order to separate by-products, the filtrate from the catalyst removal can be admixed at a temperature of 5 to 80° C. with 5 to 50% by weight active carbon in relation to the weight of the filter cake and stirred for 20 to 60 minutes. For special purity requirements this procedure can be repeated once or several times. Subsequently, in order to release the purine from its sodium salt, the pH value is adjusted to 8 to 10 by the controlled addition of an acid such as formic acid, sulphuric acid or carbonic acid during which the purine is precipitated from the aqueous solution and can be isolated by filtration. Alternatively the purine can be separated and the catalyst recovered by evaporating the obtained reaction suspension to dryness, preferably under a vacuum, and subsequently treating the evaporation residue in the same way as described above for the filtration residue.

The recovery of the catalyst during the purification of the purine enables the amount of salt formed to be considerably reduced compared to the state of the art.

The yields according to the process of the invention reach values of up to 94% of theory, the purines being obtained in purities of over 98%. Due to these high yields, the reduced formation of salts compared to the state of the art and the low technical resources, the process according to the invention is particularly well suited for a technical scale process.

The following examples are intended to elucidate the invention in more detail.

EXAMPLE 1

31.6 g (0.2 mol) 2,4-diamino-6-hydroxy-5-nitrosopyrimidine (DAHNP) were suspended in 150 ml formamide and 43.3 g.(0.8 mol) 85% formic acid. Then 1.0 g palladium catalyst on active carbon (type E10 R/W 5% Pd, 50% wet) was added while stirring vigorously during which a slow generation of gas started. The temperature was adjusted to 110° C. and held for 3 hours. The suspension which was pink at first became grey after about 2 hours. Subsequently it was heated for 3 hours at 180° C. The grey suspension which cooled to 20° C., the solid was sucked over a nutsch filter, washed three times with 50 ml water and stirred into 320 ml of a 5% by weight sodium hydroxide solution. The noble metal catalyst was filtered from the solution of the sodium salt of the guanine and washed twice with 5 ml water. The combined filtrates were heated to 50° C. and admixed with 3 g active carbon. This was removed by filtration after 30 minutes and the guanine was precipitated by slowly adding 85% formic acid up to pH 9.5. The product was isolated by filtration, washed twice with 50 ml water and dried at 80° C. in a vacuum.

28.8 g (0.188 mol, 94% of theory) guanine was obtained having a yellowish tinge and a content of 98.5% according to HPLC. No dissolved palladium was found in the mother liquor.

EXAMPLE 2

31.6 g (0.2 mol) DAHNP was converted to guanine according to example 1 using the noble metal catalyst recovered in example 1 which had been complemented with 15% by weight fresh catalyst. 28.2 g (0.184 mol, 92% of theory) was obtained in the form of a powder having a slight yellowish tinge.

EXAMPLE 3

845 g filter-wet DAHNP with a residual moisture content of 45% (3.0 mol) was suspended in 2.5 l formamide and admixed with 650 g (12.0 mol) 85% formic acid. After adding 15 g of a palladium catalyst on active carbon (analogous to example 1), the temperature was increased to 110° to 120° C. during which a strong development of $CO_2$ was observed. After about 1 hour the suspension, which was initially pink, became grey. It was stirred for a further 30 minutes at 110° C. and then about 600 ml liquid was removed by distillation until the temperature of the reaction mixture had reached 180° C. It was then heated for 3 hours at this temperature under reflux. After cooling to 60° C., 1 l of a mixture of methanol and water in a ratio of 1:1 was added and subsequently cooled to 20° C. The solid obtained was suction filtered, washed twice with 500 ml water each time and dissolved in 2.5 l 10% sodium hydroxide solution. The insoluble catalyst was separated by filtration. The filtrate was admixed with 40 g of a commercial active carbon and stirred for 30 minutes at 60° C. After separating the active carbon by means of filtration, $CO_2$ was passed into the solution until a pH value of 9.5 was reached. In this process a colorless solid precipitated, which was filtered, washed twice with 500 ml water each time and dried in a vacuum at 60° C. 426 g guanine (2.82 mol, 94% of theory) was obtained in this way as an almost colorless powder.

EXAMPLE 4

29.0 g (0.2 mol) 2,4-diamino-6-hydroxypyrimidine hydrate was nitrosed with 13.8 g (0.2 mol) sodium nitrite and 10.8 g (0.2 mol) 85% formic acid in 150 ml formamide and the pink-coloured suspension obtained was admixed with a further 42.4 g (0.8 mol) 85% formic acid. After stirring in 1.0 g of a palladium catalyst on active carbon according to example 1, it was heated for 3 hours to 120° C. In this process the suspension became colorless and was subsequently heated for 3 hours to 180° C. while removing a small amount of water by distillation. After cooling to 80° C., 100 ml water was added and the solid was suction filtered. The filter cake was washed twice with 50 ml water and dissolved in 320 ml of a 5% sodium hydroxide solution. The insoluble noble metal catalyst was removed by filtration and the filtrate was stirred for 30 minutes at 50° C. with 3 g active carbon. After separating the active carbon, guanine was precipitated by addition of 20% sulphuric acid to pH 9.0, suction filtered, washed twice with 50 ml water and dried in a vacuum at 80° C. 26.7 g (0.174 mol, 87% of theory) 98.4% pure guanine was obtained in this manner.

EXAMPLE 5

31.6 g (0.2 mol) DAHNP was suspended with 6.3 g (0.1 mol) ammonium formate and 1.0 g palladium catalyst analogous to example 1 in 150 ml 85% formic acid and it was heated for 20 hours under reflux. In this process the suspension decolorized after about 3 hours. Subsequently it was evaporated to dryness in a vacuum and the residue was dissolved in 350 ml 5% sodium hydroxide solution. After separating the catalyst and treating the filtrate as in example 1, 26.5 g (0.170 mol, 85% of theory) 97% guanine was obtained which additionally contained about 1% 2,4-diamino-5-formyl-amino-6-hydroxypyrimidine.

EXAMPLE 6

A mixture of 31.6 g (0.2 mol) DAHNP, 6.8 g (0.1 mol) sodium formate and 1.0 g palladium catalyst corresponding to example 1 was heated for 4 hours under reflux in 150 ml 85% formic acid. Subsequently the suspension was fed into a stirred autoclave and heated for 3 hours to 150° C. In this process an inner pressure of 6 to 7 bar forms. After cooling the pressure was released, the contents of the autoclave were removed and the solid was suction filtered. The filter cake was treated further analogously to example 1. 21.6 g (14.3 mol, 71% of theory)guanine was obtained with a purity of 99.4%. It was possible to obtain a further 6.2 g (20% of theory) guanine by adding sodium hydroxide solution to the residue after evaporation of the filtrate.

EXAMPLE 7

28.9 g (0.189 mol, 94% of theory) guanine with a purity of 98.9% was obtained analogously to example 1 from 31.6 g (0.2 mol) DAHNP using 1.0 g platinum on active carbon (5% Pt, 50% wet).

EXAMPLE 8

13.9 g (0.1 mol) 4,6-diamino-5-nitrosopyrimidine was suspended in 50 ml formamide, 6.8 g (0.1 mol) sodium formate, 27.0 g (0.5 mol) 85% formic acid and 0.5 g palladium catalyst were added according to example 1 and the mixture was heated for 4 hours to 110° C. The decolorized suspension was subsequently heated for 3 hours to 180° C. and then cooled. In order to improve the processing, 50 ml water was added and the solid was filtered. The filter cake was dissolved in 160 ml 5% sodium hydroxide solution and the insoluble Pd catalyst was separated. The clear filtrate was adjusted with sulphuric acid to a pH value of 8.5 after a 30 minute treatment at 50° C. with 3 g active carbon. In this process a colorless precipitate separated out from adenine which was suction filtered, washed twice with 30 ml water and dried in a vacuum at 80° C. 12.2 g adenine (0.090 mol, 90% of theory) was obtained in this way as a white powder.

EXAMPLE 9

Analogously to example 8, 15.4 g (0.1 mol) 2,4,6-triamino-5-nitrosopyrimidine was converted to 2,6-diamino purine. In this way 12.2 g (0.081 mol, 81% of theory) was obtained in the form of a pale beige colored powder.

We claim:
1. Process for the production of a compound of formula (I):

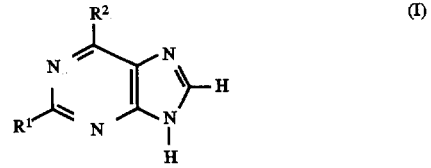

wherein $R_1$ and $R_2$ are the same or different and are selected from the group consisting of H, OH, SH, NH2, N-alkyl, N-dialkyl, halogen, O-alkyl, S-alkyl, alkyl or aryl groups, wherein the alkyl group has from 1 to 4 carbon atoms and the aryl group is a phenyl residue which is non-substituted or substituted by $CH_3$, OH, $NH_2$, or halogen; comprising reductively formylating a corresponding 4-amino-5-nitrosopyrimidine compound of formula (II)

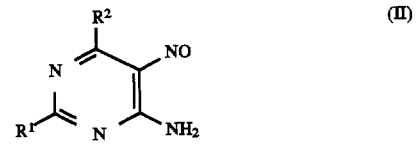

wherein $R_1$ and $R_2$ comprises the same groups as recited for Formula I in the presence of formic acid and a noble metal catalyst in a solvent at a temperature of from 80° to 220° C. to produce a 40-amino-5-formylaminopyrimidine intermediate and cyclizing said intermediate to obtain the compound of Formula I.

2. Process of claim 1, wherein the solvent is formamide or formic acid or combination of both.

3. Process of claim 1, wherein the concentration of the compound of formula (II) is 0.1 to 3.0 mol/liter.

4. Process of claim 3 wherein the concentration of the compound of formula (II) is 1.0 to 2.0 mol/liter.

5. Process of claim 1, wherein the compound of formula (II) is used together with water after it has been formed previously by nitrosation and includes sodium formate.

6. Process of claim 2, wherein the solvent is formamide and the formic acid is added in a molar ratio of 2.0 to 10.0, relative to the added amount of the compound of formula (II).

7. Process of claim 6, wherein the solvent is formamide and the formic acid is added in a molar ratio of 3.5 to 5.0, relative to the added amount of the compound of formula (II).

8. Process of claim 1, comprising formylating said compound of formula II with a solution of at least 20% by weight of formic acid.

9. Process of claim 1, further comprising adding to said reaction mixture a formate selected from the group consisting of an alkali formate, an alkaline-earth metal formate, and ammonium formate and in a molar ration of from 0.1 to 5:1 relative to the added mount of said compound of formula I.

10. Process of claim 1, wherein said noble metal catalyst is selected from the group consisting of palladium, platinum, ruthenium or rhodium, and is used in an amount of 20 to 2000 mg of the pure noble metal per kg of the compound of formula (II) used.

11. Process of claim 1, wherein said noble metal catalyst is on a carrier material, the noble metal content of which is 0.1 to 10% by weight.

12. Process of claim 11, wherein said carrier material is active carbon.

13. Process of claim 1, wherein the reductive formylation is carried out at a temperature of 80° to 140° C.

14. Process of claim 13, wherein the reductive formylation is carried out at a temperature of 100° to 120° C.

15. Process of claim 1, wherein said solvent is formamide and the cyclization is carried out by heating in a temperature range of 150° to 190° C.

16. Process of claim 1, wherein said solvent is formic acid and the cyclization is carried out by heating in a temperature range of 100° to 170° C.

17. Process of claim 16, wherein said cyclization is carried out under a pressure of up to 20 bar.

18. Process of claim 1, further comprising evaporating the solvent from the reaction mixture containing said compound of Formula I.

19. Process of claim 1, further comprising filtrating the compound of Formula I from the second reaction mixture.

20. Process of claim 19, wherein the filtration includes the addition of water or organic solvents.

21. Process of claim 18, further comprising dissolving said compound of Formula I in dilute sodium hydroxide, removing said noble metal catalyst from the dissolved product by filtration and precipitating said compound of Formula I with an acid.

22. Process of claim 19, further comprising dissolving said compound of Formula I in dilute sodium hydroxide, removing said noble metal catalyst from the dissolved product by filtration and precipitating said compound of Formula I with an acid.

23. Process of claim 21, wherein said compound of Formula I is subjected to at least one carbon treatment prior to precipitating said compound with said acid.

24. Process of claim 22, wherein said compound of Formula I is subjected to at least one carbon treatment prior to precipitating said compound with said acid.

25. Process of claim 5 wherein said compound of Formula (II) is used in a suspension.

* * * * *

UNITED STATES PATENT AND TRADEMARK OFFICE
CERTIFICATE OF CORRECTION

PATENT NO.      :   5,688,947

DATED           :   November 18, 1997

INVENTOR(S)     :   Thalhammer et al.

It is certified that error appears in the above-identified patent and that said Letters Patent are hereby corrected as shown below:

In column 4, line 20, after "which" insert -- was formed --.

In Claim 9, column 7, line 7, after "formate" delete -- and --.

Signed and Sealed this

Twenty-third Day of November, 1999

Attest:

Q. TODD DICKINSON

*Attesting Officer*      *Acting Commissioner of Patents and Trademarks*